United States Patent [19]
Guichard et al.

[11] 3,939,694
[45] Feb. 24, 1976

[54] METHOD AND APPARATUS FOR MEASURING THE CONCENTRATION OF SOLID PARTICLES SUSPENDED IN A GAS PHASE

[75] Inventors: Jean-Claude Guichard, Ris-Orangis; Claude Chauvelier, Ballancourt, both of France

[73] Assignee: Institut National de Recherche Chimique Appliquee, Paris, France

[22] Filed: Feb. 26, 1974

[21] Appl. No.: 445,927

[30] Foreign Application Priority Data
Feb. 28, 1973  France .................................. 73.07160

[52] U.S. Cl. .................................................. 73/28
[51] Int. Cl.² ........................................ G01N 33/00
[58] Field of Search ................... 73/28; 55/103, 131

[56] References Cited
UNITED STATES PATENTS

| | | | |
|---|---|---|---|
| 2,924,294 | 2/1960 | Johnstone | 55/103 |
| 2,994,035 | 7/1961 | Feifel | 73/28 |
| 3,114,877 | 12/1963 | Dunham | 73/28 |
| 3,679,973 | 7/1972 | Smith et al. | 73/28 |
| 3,680,287 | 8/1972 | Wood et al. | 55/103 |

Primary Examiner—James J. Gill
Assistant Examiner—Anthony V. Ciarlante
Attorney, Agent, or Firm—Karl W. Flocks

[57] ABSTRACT

A method and apparatus for measuring the concentration of solid particles in a gaseous phase which consists in passing a solid particles laden gas through at least one fluidized bed of balls having a diameter greater than that of the largest particles of said gas in order that said balls are not carried away by the ascending air stream. During their passage through the fluidized bed, these particles collide with the balls of the fluidized bed giving rise to a triboelectrification phenomenon and the electric current collected by the metallic walls of the container in which the fluidized bed is provided, is measured by a suitable electric or electronic control system upon separation of particles from the balls.

6 Claims, 7 Drawing Figures

FIG.2

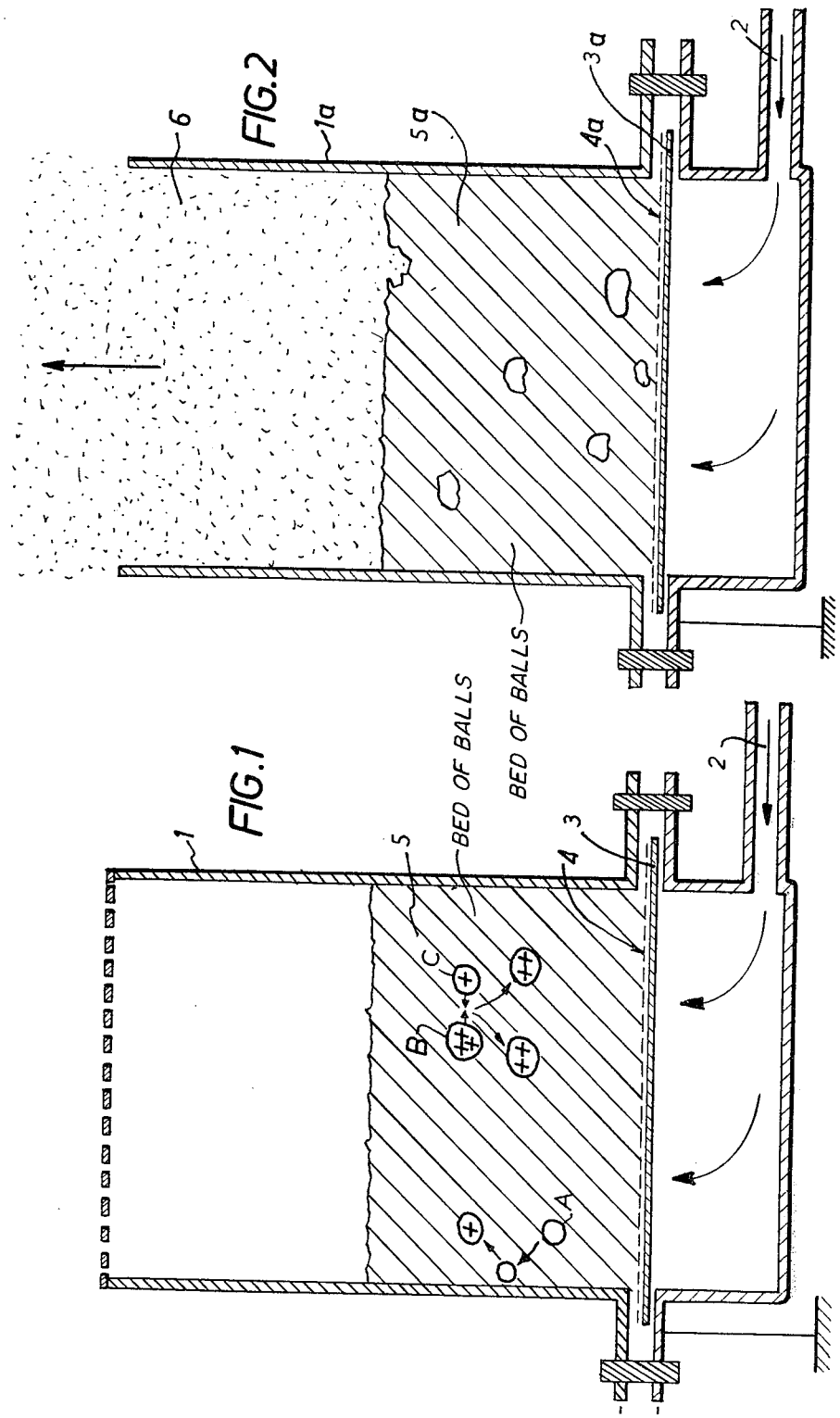

METHOD AND APPARATUS FOR MEASURING THE CONCENTRATION OF SOLID PARTICLES SUSPENDED IN A GAS PHASE

The present invention relates to a method for measuring the concentration of solid particles suspended in a gas phase of the aerosol or fume type and the design of an apparatus and an installation for applying this process.

The fight against atmospheric pollution is known to be growing in intensity at present. Legislation is being progessively set up in different countries, the first decisions taken relate to industrial discharge and, particularly, lay down the maximum allowable concentration of dusts issuing from stacks. This necessitates continuous measurement to check that these regulations are observed.

There are various devices on the market for continuous dust content measurement which have been evolved in the context of aerosol physics and adapted to the special conditions encountered in factory smoke stacks. Among these are:

— so called $\beta$-ray devices which sample the aerosol and filter it with a paper having a high separating power collecting all the suspended dust particles. In this way a "stain" is obtained whose weight is measured by its attenuation of a $\beta$-ray passing through it. Technically, this apparatus resolves the continuous measurement problem for the majority of industrial effluents; unfortunately, by its very operating principle, the cost of such systems discourages users;

— photometers or opacimeters which use the phenomenon of absorption or diffusion of light by the dust cloud in order to obtain its weight concentration. They may give rise to certain maintenance difficulties, which is a draw-back, but their major defect is that these apparatus are based on physical laws causing their response to be related to weight concentration through a certain number of parameters such as grain size distribution, colour, refraction index, etc. For each stack calibration is generally required which retains its significance during the year only insofar as the physico-chemical properties of dust vary little. If this is not the case, the recording indications are difficult to interpret in terms of weight concentration. For lack of any better solution, however, it is this equipment whose costs are bearable which is used the most.

Now, the present invention concerts a new measuring method and the apparatus and installation for applying this method, providing what the above analysis shows to be lacking, namely: a robust inexpensive device in use of which dust concentrations ranging approximately from 10 mg/m³ to 150 mg/m³ can be continuously recorded with a sufficient degree of accuracy.

The method according to the invention is based on recent knowledge concerning triboelectrification of fluidized beds, spouted beds, aerosol particles and interactions between fluidized beds and aerosol.

This knowledge is required in order to understand the present invention. However, to simplify matters, we shall confine ourselves to the particular case of oxidized or non-oxidized metallic particles, it being clearly understood that the process and apparatus according to the invention may be applied to any type of solid particle.

The invention will now be described in detail in connection with the accompanying drawings in which:

FIG. 1 schematically illustrates a fluidized bed and the phenomenon by which the balls constituting said bed are brought into a stationary state of charge;

FIG. 2 schematically illustrates how a fluidized bed can be used as an aerosol generator;

Figure 3:
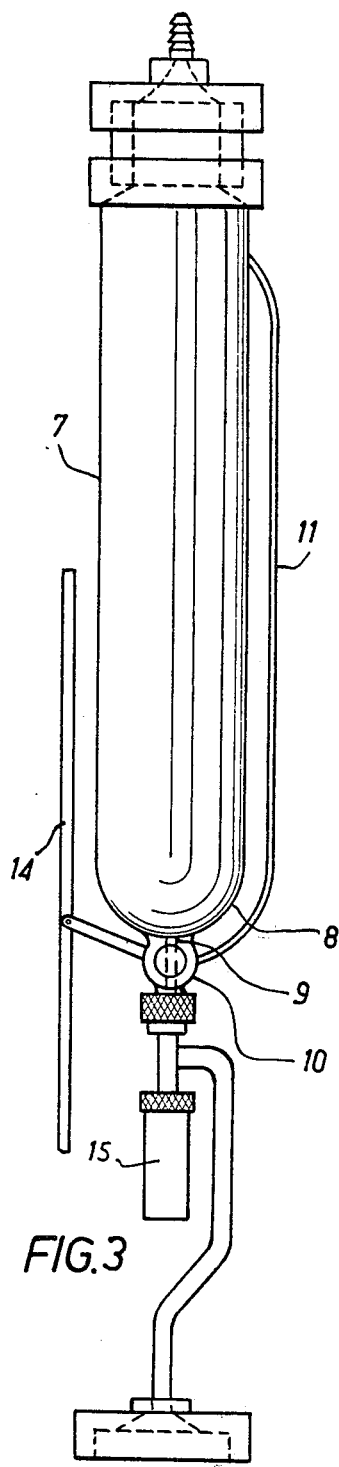
FIG. 3 shows one of the stages of an apparatus in accordance with the invention.
Figure 4:
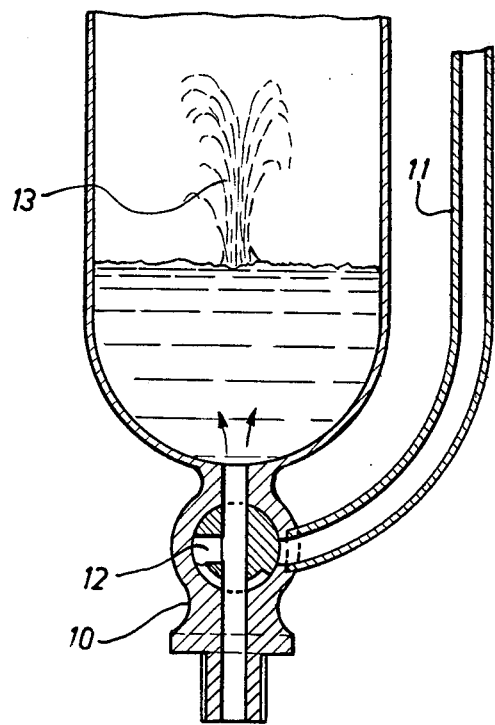
FIG. 4 illustrates in a larger scale a spouted bed obtained in the apparatus of FIG. 3.
Figure 5:
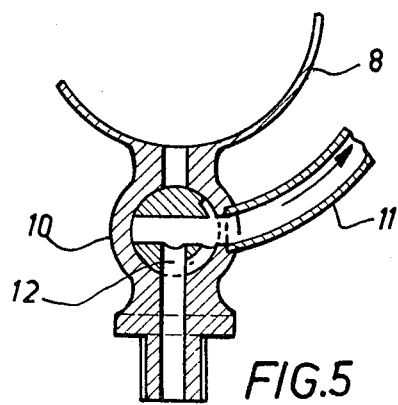
FIG. 5 is a part of FIG. 4 in another position.

Assuming now a bed of metallic particles of the same dimensions fluidized in a container, which is also metallic, comprising an air intake grating of the same material as the container wall.

In a first approximate description, this bed may be likened to a collection of particles in almost-Brown ion type movement in which they collide with one another and with the walls. If the particles are all of the same material, their collisions do not lead to any particular electrical phenomena, except equal distribution of the charges contained before impact. On the other hand, when they strike the wall, which is assumed to be of a different metal (for example copper balls in a stainless steel container), an electrostatic charging phenomenon is caused owing to the existence of a potential difference on contact. This explains why, after separation, the ball is charged while the wall has received an equal charge of opposite polarity. In this way, FIG. 1 of the attached drawings represents a fluidization container 1 in which an air current admitted at 2 passes through a microporous membrane 3 then a metallic grating 4 and fluidizes the bed of balls 5 wherein the balls each are of such small diameter in comparison to the apparatus so that they are depicted only as a mass in the figures. After impact with a wall of the container, a ball such as A shown greatly enlarged is initially charged (for example positively) while an equal opposite charge (for example negative) remains on the fluidization container wall. The charge is directly proportional to the difference in the extraction potentials between the two metals in question and that one with the lower value is positively charged. When one of the metals is superficially oxidized, it can be demonstrated that it behaves like a semi-conductor and that it always charges the opposite metal with the same polarity whatever the latter may be. If it is of the n-type it supplies electrons, if it is of the P-type it produces positive charges on impact. In this same FIG. 1, collision between the particles such as B and C leads to equal charge distribution.

Thus, taking a bed composed initially of neutral particles, if it is fluidized in the container under total effect, it can be understood that as a result of electrifying impacts against the walls, impacts which are followed by charge equaiization with the neighbouring particles, the bed finally reaches a state of stationary electrostatic charge. In this state, each particle possesses the charge that it is liable to acquire when in collision with a wall. Furthermore, whether it is directly earthed or earthed through a measuring instrument, the fluidization container possesses, on its internal surface, a charge equal to and opposite that of the bed.

Supposing for a moment that, in the bed which has reached its stationary charge state, there is a mechanism capable of cancelling out the charge in a given ball, the equivalent quantity of electricity which was maintained by influence on the wall will immediately flow to earth or the measuring instrument. Then, the neutral ball will be recharged by colliding with neighbouring balls or the container. This return of the bed to stationary electrical equilibrium does not give rise to any current flow. Hence, if there is a system in the bed that is capable of continuously discharging the balls, a direct current to earth or the measuring instrument should be observed. It is important to point out that the system then constitutes a high internal impedance current generator, as it is known that the fluidized bed, even one constituted of metallic balls, is a fairly insulating medium. It will also be noted that analogous phenomena occur in the case of partial ball discharge, or, on the contrary, a new charge added to the existing one, whether it be positive or negative.

Thus, for example, if a mixture (5a) of balls of a few hundreds of microns and a small quantity of fine powder whose particles adhere to the surface of these balls is introduced into a container 1a (FIG. 2 of the attached drawings) designed like the container of FIG. 1 for fluidization by air admission at 2 below the metallic grating 4a associated with micro-porous membrane 3a, and if this entity is fluidized, the required air flow rate is governed by the weight of the balls and this results in air velocities, through and over the bed, which are far greater than the fine particle elutriation velocity. Thus, when these particles are detached on impact or as a result of localized aerodynamic turbulence, they are removed in the form of an aerosol 6 whose concentration is a function of the fine powder content of the bed. But this mixture is capable of storing an electric charge as above mentioned. If it is assumed that separation takes place without the occurrence of triboelectrical phenomena, the aerosol particles continuously remove a part of the charge from the bed and as a result a current flows from the fluidization container, this current being equal to that discharged by the aerosol. If triboelectrification takes place when the fine particles are separate, the previous charge is modified (it may, in an extreme case, be nil if triboelectrification releases an equal charge of opposite polarity to that already existing on the particle), but there will always be an electric current related to the concentration of dust particles removed. Furthermore, it may be supposed that, instead of fluidizing a bed of particles (some hundreds of microns in diameter) with clean air, a dust laden gas is used. It is first noted that, apart from a short balancing phase, an aerosol of the same concentration as at the input is released. This system can then function indefinitely without clogging since there is no dust accumulation in the bed. On first reflection, it might be thought that the particles simply directly cross the fluidized layer. In reality, experience shows that the majority of them are collected, that they remain adhering to the balls for a certain time, and then they are re-emitted, as in the case of the above described fluidized bed with two constituents. The collecting efficiency of the fluidized bed is a function of many parameters including dust particle dimension, ball dimension, fluidization rate, the height of the layer to be crossed, electrical forces, etc. The question is far from resolved, but it can be said that it is technically possible to produce systems in which collection is "quantitative" when the level of 1 or 2 microns is exceeded. Finally, charge transfer when the aerosols are fixed is added to the electrical phenomena above mentioned.

It should be pointed out that the above considerations concerning fluidized beds hold good, subject to certain adaptations, for the spouted bed. This bed, which is closely related to the fluidized bed, is obtained in a hemispherical or conical base column pierced by an air intake orifice. It is filled with balls of some hundreds of microns and air is passed through. If the experimental conditions are well selected, in the centre of the layer appears a sort of spout of balls strikingly similar in appearance to a water-spout. This spout constitutes the upper portion of a central column wherein there is a system of balls in suspension according to a vertically rising rate. Around this column, a fixed bed slowly lowers and supplies its lower portion.

One possible form of embodiment of a spouted bed is illustrated by FIGS. 3 to 5. These represent column 7, its hemispherical base 8, the air intake orifice 9. A device enabling the spout to be started and stopped easily is constituted by a valve 10 of the "municipal gas" needle type. A third duct which travels round the container through a pipe 11, is laterally open on the body of said valve. The needle 12 is so modified as to enable air to be blown directly into the bed, a spout 13 being formed, or to bypass it, depending on its position. A lever handle type control 14 serves to actuate the valve 10.

The method according to the invention thus consists in passing the aerosol to be analyzed through a fluidized bed of balls whose diameters are greater than those of the largest dust particles or through a spouted bed, and in measuring the intensity of the currents flowing from the walls of the container housing the bed and generated by the passage of the particles which are collected by the balls of the bed, then re-emitted, this intensity being proportional to the weight concentration of the aerosol.

This method may be applied whatever the gas or vapour containing the aerosol, the nature of the latter, the nature and quality of the balls constituting the bed, the nature and design of the container housing the fluidized bed or the spouted bed.

For better understanding of the value and advantages of the invention we shall take the case of a bed of metallic balls and an aerosol of equally metallic particles. The fluidization container is constructed of a single metal such as, for example, brass or stainless steel.

In order to obtain a good fluidized bed air must be blown into it or sucked through a support having a pressure drop of the same order as the bed. This is why very fine meshes or porous layers are generally selected. It is clear that if the aerosol is forced through this type of support it is quickly clogged and the system ceases to function.

A first solution consists in fluidizing the bed starting with clean air and injecting the aerosol to be analyzed into it through a lateral orifice. But the drawback of this system is its low sensitivity in relation to that obtained when using the whole bed. Another way of resolving the problem consists in using a fixed bed of balls where the diameter and weight are greater and placed on a wide mesh grating. Indeed a fixed bed is generally a packing of balls supported by a mesh and, in this particular case, the weight of any ball is chosen so that the ball remains motionless at the air velocity used to obtain the supported fluidized bed. Dust is deposited in this particular support, but when clogging has reached a certain stage, besides dilatation of the fixed bed, the dust deposited is seen to be removed, which causes current surges or peaks. This system is therefore suitable for analyzing mean concentration values in time.

In many cases, the most practical system is the spouted bed. Indeed, air is, in this case, introduced through a simple tube whose diameter precludes any likelihood of obstruction.

The functioning of the above described system can be represented mathematically. In order to do so, we shall consider the very simple case of a fluidized bed of mono-dispersed balls through which passes a mono-dispersed aerosol with a numerical concentration $C$, with a flow rate per second of $Q$ cm$^3$. It will be assumed that the initial aerosol is not charged and that it is collected with an efficiency $R$ as it passes. It will also be assumed that, during the separation of the aerosol particle from the ball carrying it, there is no triboelectrification and that it takes only a fraction the charge, or $q$ (this charge being immediately recovered by triboelectrification on the wall). Hence, $C \times Q \times R$ particles per second are concerned by this phenomenon. They remove a quantity of electricity $C \times Q \times R \times q$ and the compensating current flowing towards the measuring instrument is $i = -C \times Q \times R \times q$. If all the particles initially carry a charge $a$, the portion $C \times Q \times (1 - R)$ which has not been arrested does not feature in the electrical results. The fraction collected enters with charge $C \times Q \times R \times a$ and emerges with $C \times Q \times R \times q$. whence current flow:

$$i = -C \times Q \times R \times (9 - a).$$

This equation shows that the current released by the system is generally a function not only of aerosol concentration but also of its charge which is rarely known and which is most often high and variable (for example behind an electrical duster). However, in the case of neutral aerosols or those with the Boltzman equilibrium ($a << q$), the single measurement stage version is suitable.

In the most general case, an apparatus with two stages in series must be used as will be described below.

Assuming two measuring elements, each characterized by efficiency values $R1$ and $R2$, values $q1$ and $q2$ for charges removed by each aerosol particle. The first element encountered in the air flow direction grounded. It is completely isolated from the second which is connected to the measuring instrument. The aerosol passing through this measuring element is composed of two parts:

that not arrested by the first stage the charge of which is $C \times Q \times (1 - R1) \times a$;

that which has been collected and then re-emitted with the charge $C \times Q \times R1 \times q1$.

Each of these aerosol fractions is arrested with the same efficiency $R2$ by the measuring stage and, by applying the above reasoning, the following is obtained for the corresponding currents:

$$i_1 = -C \times Q \ (1 - R_1)R_2 \ (q_2 - a)$$
$$i_2 = -C \times Q \times R_1 R_2 \ (q_2 - q_1)$$

whence all $I = i_1 + i_2$ i.e.:

$$I = -C \times Q \times R_2 \times [\ (q_2 - R_1 q_1) - a(1 - R_1)\ ]$$

It can therefore be seen that electrical response for a unit applying the process according to the invention is practically independent of the initial aerosol charge, on condition that the first stage is efficient ($R1$ approximate to 1) or again that ($q_2 - R_1 q_1$) is large in relation to $a$. In order to obtain this last condition, it is advisable to use sucessive beds being charged with a different polarity. This also increases the intensity of response as a function of concentration $C$. This response is greater than with a single stage, especially if R2 is high.

It follows that the measuring instruments used to apply the process according to the invention will be constituted as follows:

in certain simple cases, a fluidized bed or a spouted bed in a container, generally metallic, connected to a simple amplifier circuit (or to a high impedence current source) supplying a recorder or an indicator apparatus. The whole unit is placed in a Faraday cage. The aerosol may be introduced by blowing (case of a pressurized duct or of using an intermediary compressor) or by suction when the apparatus output is connected to a vacuum source (aspirator, filter pump, etc.,) ;

more generally two stages as above series connected and electrically insulated. The first stage (in the air flow direction) is earthed and the second is connected to the measuring instrument. The instrument is placed in a Faraday cage. The balls for each bed are selected and may be of a varied type so that the electrical resonse is high and independent of the initial aerosol charge.

The instruments thus designed are simple and robust. They may be supplied with aerosols through a sampling probe or directly placed in the dust laden current.

The form of embodiment of a device according to the process of the invention is given for explanatory non-limitative purposes. The type of the material used, dimensions and, more generally, any indications concerning the design of a device are only given for the purpose of example.

The device designed in accordance with the invention is of the series connected two-spouted beds type, it is represented diagrammatically in FIG. 6 of the attached drawings. The two stages X and Y in this figure, which constitute the device each correspond to a bed and are identically constructed; they differ only in the nature of the balls that they contain.

Each stage, partially described in connection with the example given of a spouted bed, is basically composed of three parts : fluidization container, injector valve and a ball recovery device (FIGS. 3, 4 and 5).

The container is a brass cylinder, 30 cm high and 5 cm in diameter, its base is a hemisphere to which is welded an injector valve. The latter and the pot are co-axial.

The injector valve, which is also of brass, is of a "municipal gas" type with a modified needle as above indicated. The needle is so designed that control 14 can be switched from standby to operating position without the particle laden gas flow being blocked. In the standby position, the valve prevents the balls from falling. On its lower portion, the injector is connected to the recovery device (reference 15 of FIG. 3). The latter constitutes a safety means when, by accident, the gas flow is abruptly stopped (electricity breakdown, etc.,). Indeed the balls then fall into lower container 15 where they are collected.

The balls constituting the beds have the same grain size distribution obtained by screening between 400 and 500 microns using an AFNOR type screen. The lower stage (Y) contains 62 g of bronze balls, and the upper stage (X) 63 g of tin granules.

The two stage unit is enclosed in a cylindrical box 19 (FIG. 6) serving as a Faraday cage. Each stage constitutes a device that is electrically insulated by means of couplings and components of insulating materials (for example carbon polytetrafluoride). The lower stage (Y) is connected to earth (T) and the other (X) which is the measuring call properly speaking, is connected to the operating device which may include either an electrometer 16 or, through an electronic circuit, a recorder 17 or a panel indicator. The electronic circuit 18 which is composed of a transistor MOS and a high resistor, behaves as an impedance adaptor and a very simple electronic system suffices. It will finally be noted that the valves are coupled by an insulating rod and that they are simultaneously controlled by handle 14 (FIG. 6) located outside the Faraday cage.

Figure 6:
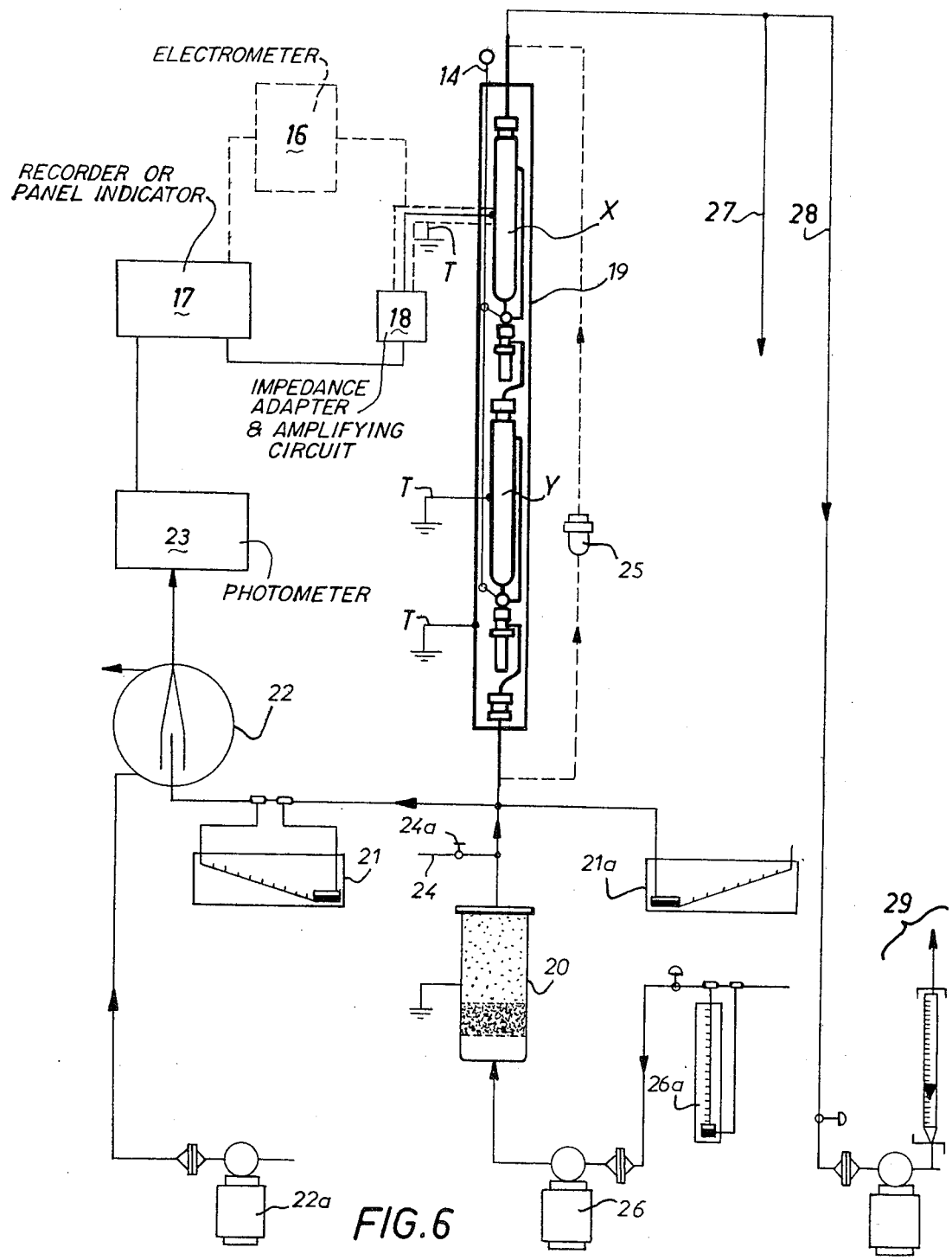
FIG. 6 is a flow diagram of an installation using an apparatus in accordance with the invention.

The form of embodiment illustrated in FIG. 6 represents various accessories for measuring and determining the desired results; these are, basically : an aerosol generator and an aerosol concentration photometric measuring device.

The aerosol generator 20 is constituted by a container housing a double fluidized bed; this device, which has already been described, is illustrated in FIG. 2. The fluidizing air is admitted through pump 26 and its flow rate is given by flow meter 26a. The particles generated can be insulating or metallic. A fraction of the aerosol is drawn in by the device according to the invention, another fraction whose flow is measured (flow-meter 21), is sent after dilution into container 22 supplied with clean air by pump 22a, towards photometer 23 the readings of which are recorded (double channel recorder 17). The excess aerosol escapes into the atmosphere (duct 24 with valve 24a). A pressure gage 21a is used to control pressure in the device by acting upon valve 24a of conduit 24. Furthermore, the output of upper stage X is connected on one hand by pipe 27, to a filter pump (not represented) and, on the other hand, by pipe 28 to the flow rotameter of device 29.

Dust concentrations are measured by filtering on a microporous membrane (membrane holder case 25) which is weighed before and after the sampling in order to determine the weight collected. The photometer which is shunt connected with the device to be tested enables any variation in aerosol emission to be detected at once and also enables concentration development to be followed for long periods. By using the device and installation as above described, it has been possible to carry out tests with a silica aerosol covering the grain size distribution range of 1 to 20 microns with a median weight of between 5 and 7.5 microns; the aerosol concentration may be selected between 10 and 1000 mg/m³, the flow through the measuring instrument being 20 l/min. The above details concerning the aerosol are given only for purpose of example.

A description of a complete cycle of operation of a preferred embodiment is as follows with reference to FIG. 6.

At first the apparatus is at rest. The aspiration or suction is started through the pipe 28 and, at the same time, the valves for the admission of air through the two stages are opened by acting on the handle 14. The flow rate of the exhausted stream is controlled by acting on the pump with its rotameter device 29 in order that the fluidized bed operates accurately.

The amplifying electronic circuit 18 is switched on as well as the recorder 17.

The aerosol is generated by the generator 20. The aerosol flow rate admitted in the apparatus 19 is controlled by acting on the valve 24a. It is adjusted in order that it will be equal to the exhausted flow rate.

In the first stage Y the aerosol particles collide the bronze balls. During this collision which is followed by their re-emission, the particles lose their initial charge and, by triboelectrification, carry in their re-emission, a new charge which is proportional to their weight. The value of the resulting current is the algebraic sum of the discharge current of the aerosol and of the current which counterbalances the electric charge carried away by the aerosol. This resulting current is left to flow directly to the earth. The tin balls of the stage X collect in their turn the particles in suspension then reemit them. During the collection the greater part of the charge imparted by the stage Y is transferred to the balls of the bed of stage X and then, through the wall of the fluidization container, the current flows through the electrical measuring device connected in series. During the re-emission of the aerosol a new electric charge appears by triboelectrification so that the quantity of electricity carried by the solid particles is different from that initially carried out at the inlet of stage X since tin balls have replaced the bronze balls.

The new electric charge is proportional to the weight of the particles. The electric current flowing is the algebraic sum of the current due to the initial discharge and of the current counterbalancing the electric charges carried by the aerosol leaving the stage X; it remains proportional to the weight concentration of the aerosol particles. This current is amplified in 18 then flows through the recorder 17.

In a first series of tests, the incoming aerosol was first given a high positive charge and then a high negative charge by contact with a unipolar cloud of small ions. The current response of the device according to the invention remains the same to within a few percent.

Long term emission was then tested (several days to several weeks) at different concentrations which were maintained constant. The response recorded remains fixed in each case. Furthermore, no clogging was observed.

Figure 7:
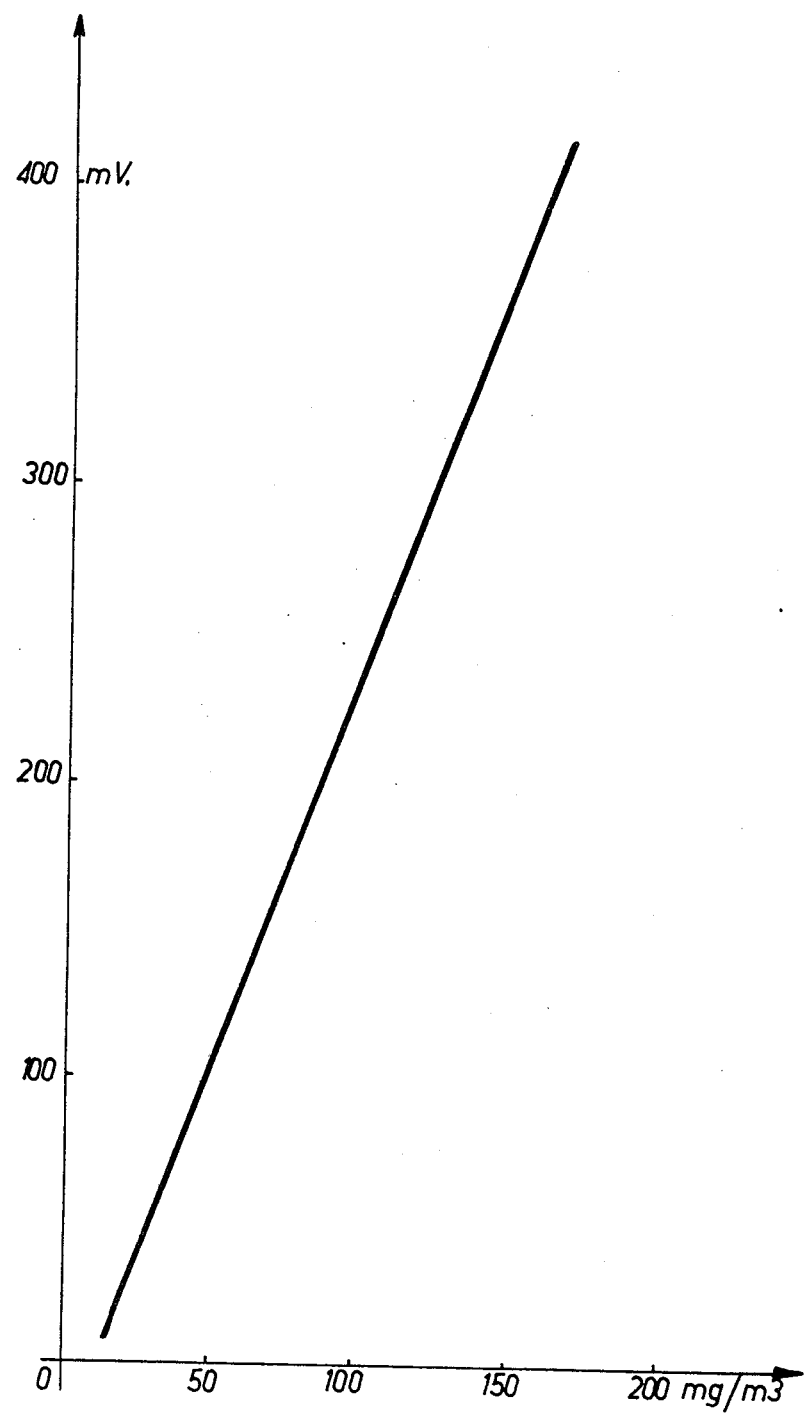
FIG. 7 is a graph showing the correlation between the MV response of the measuring device and the weight concentration of the solid particles contained in a silica aerosol.

On the basis of the tests and results obtained, a graph (see FIG. 7) was drawn up showing the correlation between the MV response (ordinate access) of the device and the weight concentration (abscissa) of a silica aerosol, expressed in mg/m³. The result is a straight line, as the brief theoretical passage in the above description suggests.

The present invention is understood to have been described only for purely explanatory, non-limitative purposes and any useful modification may be made thereto without departing from its scope such as defined in the following claims.

We claim:

1. A method for measuring the concentration of solid particles suspended in a gaseous phase comprising the steps of
   fluidizing at least one bed of solid balls placed in a metallic container, with the balls having diameters and weights greater than those of the largest particles of said gaseous phase, by admitting at its bottom a stream of said gaseous phase;
   recording a current of an intensity proportional to the weight concentration of the solid particles of said gaseous phase during separation of particles from the balls with a recorder connected through an amplifier circuit connected to the wall of said metallic container.

2. A method in accordance with claim 1 wherein the fluidizing effect of said stream of gaseous phase promotes a fluidized bed of said solid balls.

3. A method in accordance with claim 1 wherein the fluidizing effect of said stream of gaseous phase promotes a spouted bed of said solid balls.

4. A method in accordance with claim 1 wherein said container is surrounded and isolated by a Faraday cage.

5. A method in accordance with claim 1 wherein said bed of solid balls is supported on another bed of solid balls placed on a mesh grating with said latter-mentioned solid balls having a diameter and weight greater than those of said solid balls which are adapted to be fluidized.

6. A method in accordance with claim 5 wherein said another bed of solid balls placed on mesh grating are fixed bed of solid balls that remain motionless.

* * * * *